United States Patent

Brown et al.

Patent Number: 5,827,312
Date of Patent: Oct. 27, 1998

[54] MARKED CANNULA

[75] Inventors: Michael G. Brown, The Woodlands; Perry C. Forrester, Houston; Manuel C. Guyot; Stephen L. Barrett, both of The Woodlands, all of Tex.

[73] Assignee: Instratek Incorporated, Houston, Tex.

[21] Appl. No.: 909,697

[22] Filed: Aug. 12, 1997

Related U.S. Application Data

[63] Continuation of Ser. No. 488,514, Jun. 9, 1995, abandoned.

[51] Int. Cl.⁶ .................................................. A61B 17/32
[52] U.S. Cl. ............................ 606/167; 606/79; 604/164
[58] Field of Search .................................... 606/167, 170, 606/190, 166, 79, 185; 604/165, 166, 104, 164; 128/760, 772

[56] References Cited

U.S. PATENT DOCUMENTS

| | | | |
|---|---|---|---|
| 3,472,232 | 10/1969 | Ear | 604/165 |
| 4,799,495 | 1/1989 | Hawkins et al. | 128/754 |
| 4,874,376 | 10/1989 | Hawkins, Jr. | 604/165 |
| 4,986,279 | 1/1991 | O'Neill | 604/164 |
| 5,029,573 | 7/1991 | Chow | 600/104 |
| 5,063,930 | 11/1991 | Nucci | 128/760 |
| 5,190,548 | 3/1993 | Davis | 606/79 |
| 5,253,653 | 10/1993 | Daigle et al. | 128/772 |
| 5,269,290 | 12/1993 | Barrett et al. | 128/4 |
| 5,323,765 | 6/1994 | Brown | 600/104 |
| 5,620,446 | 4/1997 | McNamara et al. | 606/170 |

*Primary Examiner*—Robert A. Hafer
*Assistant Examiner*—Justine R. Yu
*Attorney, Agent, or Firm*—Browning Bushman

[57] ABSTRACT

A marked cannula is disclosed that provides for first and second indicia for marking positions along the inner surface of the cannula. The first and second indicia are distinctive with respect to each other and are easily detected or visible using an endoscope. The first and second indicia are preferably provided at positions that are representative of the general population in terms of location of the plantar fascia. The indicia provide a quick visual reference for the positioning of a surgical instrument within the bore of the cannula.

11 Claims, 2 Drawing Sheets

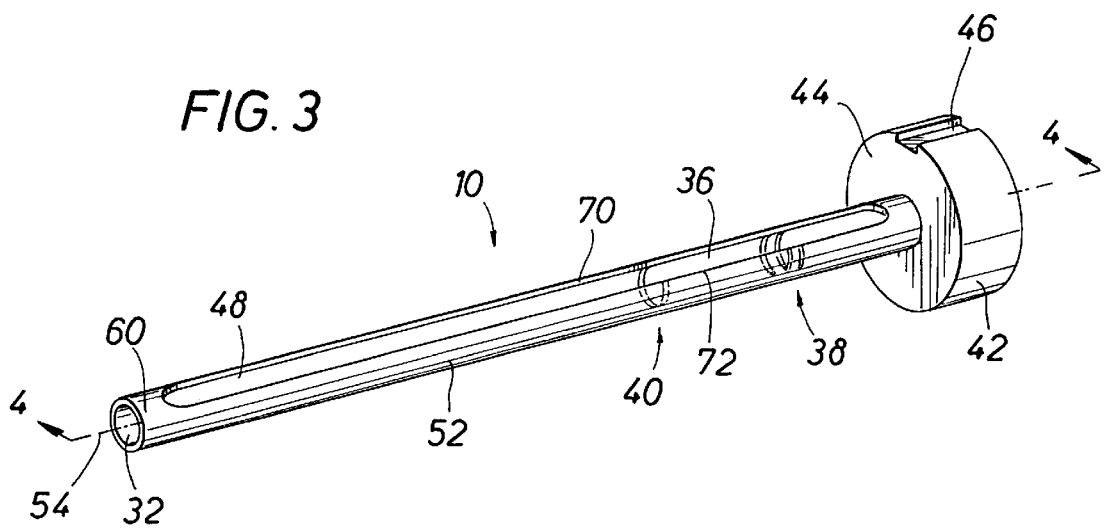
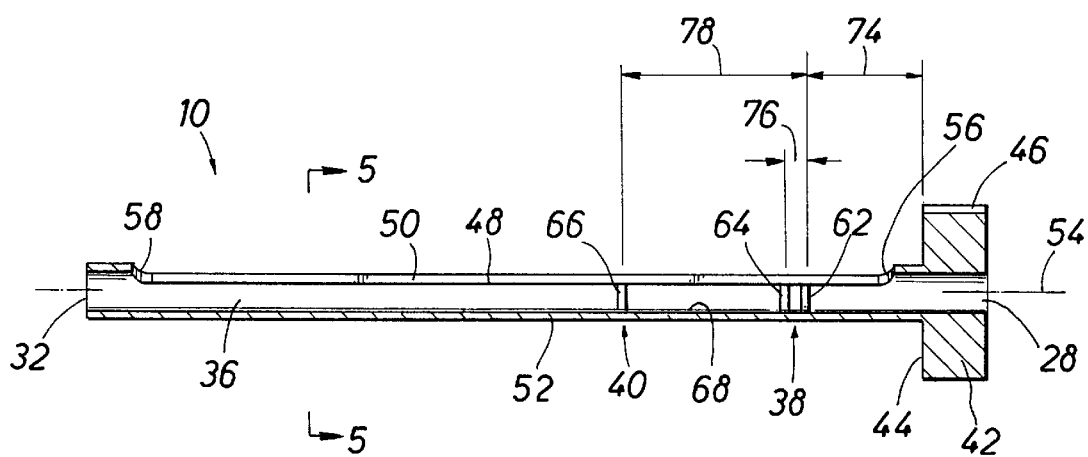
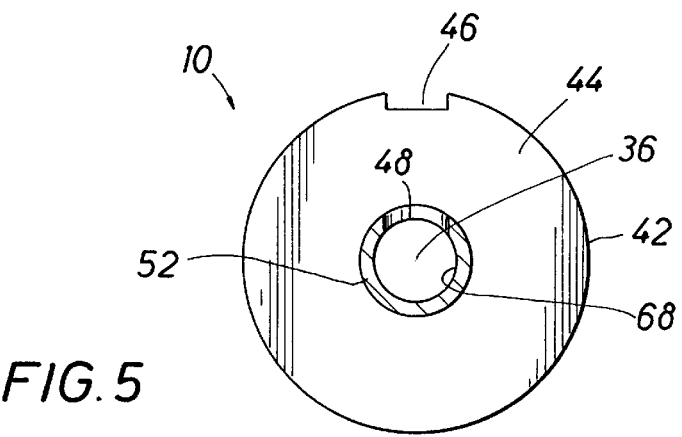

MARKED CANNULA

This application is a continuation, of application Ser. No. 08/488,514 filed Jun. 9, 1995, now abandoned.

BACKGROUND OF THE INVENTION

1. Field of the Invention

The present invention relates generally to cannulas and, more particularly, to a cannula having an indicium that is visible through an endoscopic camera inserted into the bore of the cannula.

2. Description of the Background

Many surgical techniques, such as the Barrett-Day endoscopic plantar fasciotomy surgical procedure (see U.S. Pat. No. 5,269,290) to relieve symptoms of heel spur syndrome, make use of a slotted cannula instrument for performing surgical procedures. For instance, a slotted cannula and trocar may be inserted into a channel within a body member, such as the foot, and used to penetrate completely through the body member and exit therefrom. The trocar may then be removed and an endoscope may be inserted into the cannula through one portal of the cannula. A surgical instrument may be inserted through the other portal of the cannula. The endoscope provides a view for the surgeon through the slot as the endoscope is moved back and forth in the slot or bore for viewing of the portion of the body, e.g., the plantar fascia, upon which work is performed.

As in the case of most operations, it will be appreciated that the best possible accuracy is desired. Indeed, the more accurate the surgery, the fewer complications that result. It is also desirable that the operation be performed as quickly as possible, preferably in a period of less than about 10 minutes. To ensure accuracy and minimize time of operation, proper positioning of the cutting instrument relative to the fascia is imperative. For instance, it is generally desirable to cut only a portion, usually a third, of a plantar fascia. Therefore, it is desirable to have some means for knowing the position of the cutting instrument with respect to the fascia.

However, when one is viewing the interior of the foot through the endoscopic camera that is positioned within the bore of the cannula, the bore of the cannula may have only a relatively small portion thereof visible at any one time. Thus, the axial position of the surgical instrument in the cannula bore may be difficult to quickly and accurately determine with respect to the view from the endoscope. Moreover, the portion of the body viewed endoscopically through the cannula slot may not always be particularly distinctive over the region at which work is to take place. In other words, the region viewed by the endoscope may not provide a visual frame of reference to allow the surgeon to quickly position his instrument. In such a case, it may be somewhat time consuming to make and monitor measurements, as from probing instruments, for the position at which work is to be made. Thus, it is desirable in many cases to be able to quickly and easily position the surgical instrument at a particular position within the bore of the cannula, preferably by conveniently viewing through an endoscopic camera.

Consequently, there remains a need for instruments that provide the ability for the surgeon to quickly, easily, and— most importantly—accurately determine the relative position of a surgical instrument within a cannula while viewing through an endoscopic camera. Those skilled in the art have sought and will appreciate the present invention, which provides solutions to these and other problems.

SUMMARY OF THE INVENTION

The marked slotted cannula of the present invention may be used with an endoscope for readily positioning a surgical instrument at a desired position along the length of the bore in the cannula while viewing through the endoscope.

Therefore, the present invention relates to a cannula that is operative for receiving an endoscope. The cannula comprises a tubular body having an internal surface defining a bore of the tubular body. The tubular body has a tubular body wall and a tubular longitudinal axis. The tubular body defines an elongate slot through the tubular body wall such that the elongate slot is parallel with the tubular longitudinal axis.

A first indicium is disposed at a first position along the internal surface of the bore adjacent the elongate slot. The first indicium is visible through the endoscope for designating the first position along the internal surface of the bore.

A second indicium is disposed at a second position along the internal surface of the bore adjacent the elongate slot. The second indicium is axially spaced from the first indicium. The second indicium is visible through the endoscope for designating the second position along the internal surface of the bore. The first indicium and the second indicium are preferably visibly distinctive from each other when viewed with the endoscope.

A flange member is typically disposed on one end of the tubular body such that it is substantially orthogonal with respect to the tubular longitudinal axis. The first indicium is medial to the flange member and the second indicium is distal to the flange member.

It is an object of the present invention to provide an improved cannula.

It is another object of the present invention to provide a cannula that provides a frame of reference for positioning a surgical instrument when the bore of the cannula is viewed through an endoscope.

A feature of the present invention is first and second indicia disposed within the bore of the cannula to visibly mark selected positions within the bore.

Another feature of the present invention is indicia that are marked with a laser.

An advantage of the present invention is that the surgeon may more accurately and easily position a surgical instrument at a desired location by viewing through the endoscope.

These and other objects, features, and advantages of the present invention will become apparent from the drawings, the descriptions given herein, and the appended claims.

BRIEF DESCRIPTION OF THE DRAWINGS

FIG. 3 is a perspective view, partially in phantom, of a slotted cannula with indicia in accord with the invention;

FIG. 4 is a cross-sectional view, in section, of the slotted cannula of FIG. 3 along line 4—4; and FIG. 5 is a cross-sectional view, in section, of the slotted cannula of FIG. 4 along line 5—5.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

DETAILED DESCRIPTION OF THE PREFERRED EMBODIMENTS

Figure 1:
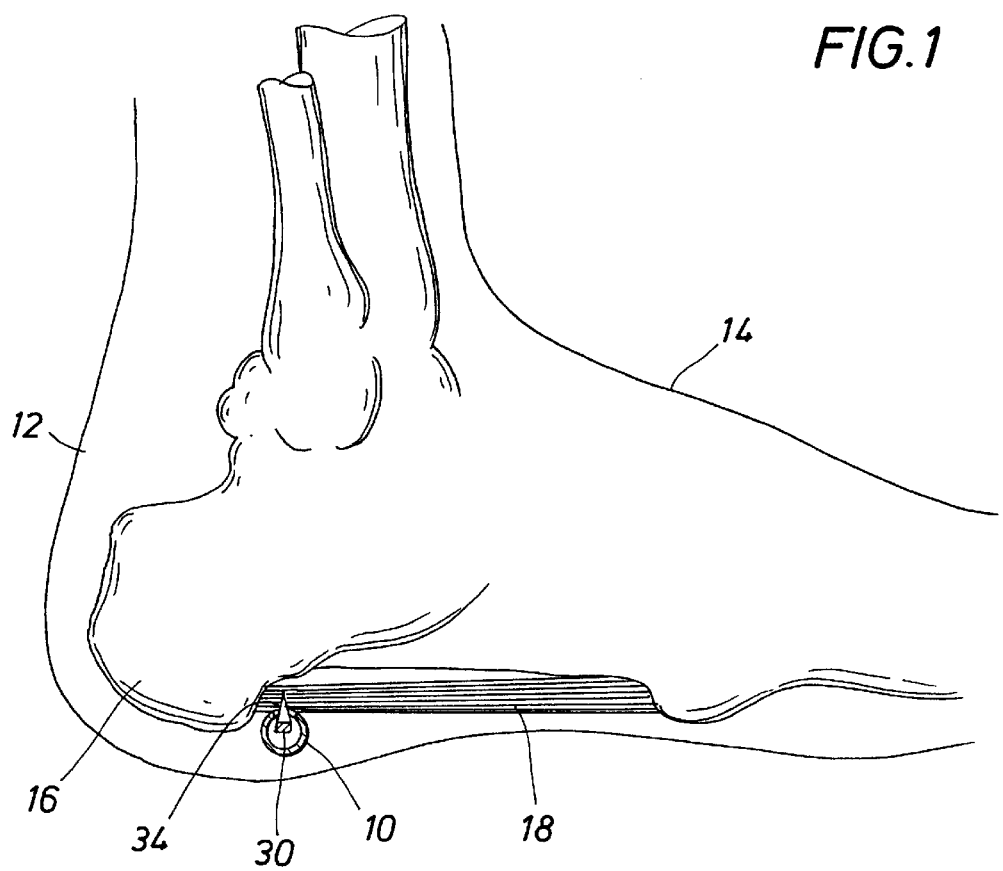
FIG. 1 is an elevational view, partially in section, of the plantar fascia within a foot and a cutting instrument positioned within a slotted cannula for cutting at least a portion of the plantar fascia.
Figure 2:
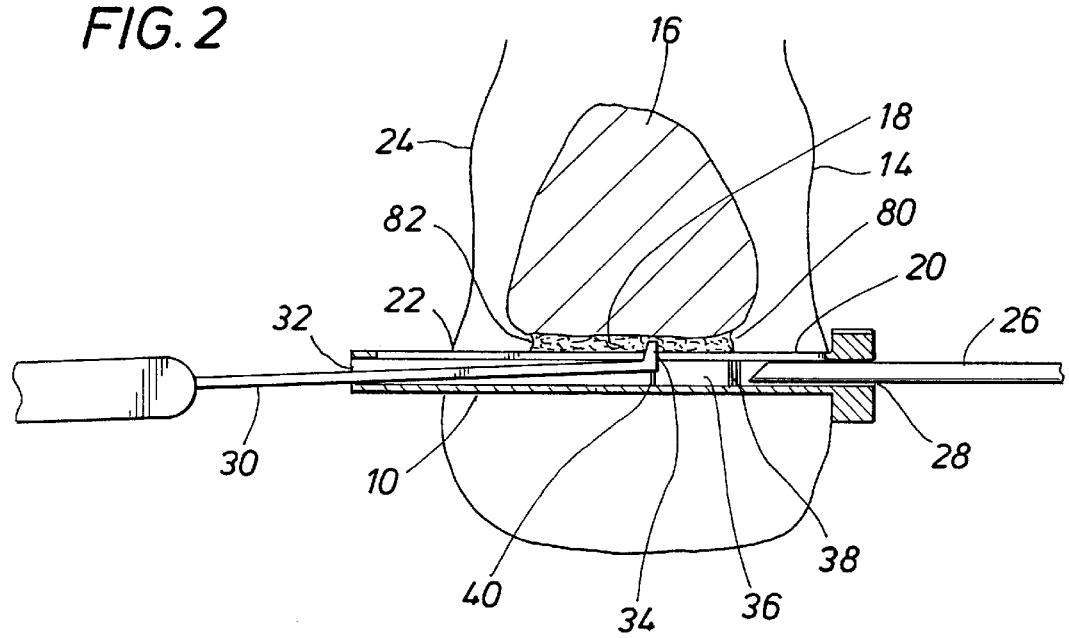
FIG. 2 is a cross-sectional view, partially in section, of the plantar fascia of FIG. 1.

With reference now to the drawings, and more particularly to FIG. 1 and FIG. 2, cannula 10 is illustrated in position for use in a plantar fasciotomy surgical procedure in accord with the present invention. An exemplary procedure of this type is described in U.S. Pat. No. 5,269,290 to S. L. Barrett and S. V. Day and is incorporated herein by reference. Although it is contemplated that the cannula of the present invention would have uses in other types of surgical procedures, the advantages of the present invention may be conveniently understood in terms of the plantar fasciotomy procedure.

FIG. 1 illustrates schematically a side view of heel portion 12 of foot 14. Foot 14 includes a number of connected bones including heel bone 16 that is located generally rearwardly and downwardly in foot 12. Heel bone 16 connects to plantar fascia 18, which is substantially a dense band of tissue that extends forwardly from heel bone 16 and spreads out among the toes.

Very generally, channel 20 within foot 14 is formed with surgical instruments, and a trocar (not shown) and cannula 10 are placed into channel 20 along the inferior surface of plantar fascia 18. Once the trocar can be palpated through the skin, a second incision 22 is made on lateral side 24 of foot 12 so that the trocar and cannula extend through foot 14, as shown in FIG. 2.

Endoscope 26 may then be inserted through medial portal 28 for viewing while surgical instrument 30 is inserted through lateral portal 32 for incision with blade 34.

If it is intended to provide only a partial incision in plantar fascia 18 rather than a complete fascial release, then it is desirable to have some additional means for referencing the position of blade 34 relative to bore 36 of cannula 10. Indicia 38 and 40, shown more clearly in FIG. 3 and FIG. 4 and discussed in detail hereinafter, are provided in bore 36 of cannula 10 to allow visual position referencing of blade 34 within bore 36 using endoscope 26. Bore 36 has a diameter sized to receive endoscope 26 and preferably maintains a constant diameter throughout its length through cannula 10.

In FIG. 3 and FIG. 4, cannula 10 is provided with flange member 42, having surface 44 for engagement with foot 14. Alignment groove or marker 46 may be provided to allow visual indication of orientation of elongate slot 48. Elongate slot 48 is provided through wall 50 of cannula body 52 and extends along wall 50 in parallel with cannula body axis 54 through bore 36. Elongate slot 48 provides visual and instrument access to plantar fascia 18. Medial end 56 adjacent flange 42 and distal end 58 of slot 48 of cannula 10 are the end points of slot 48 in the presently preferred embodiment. Indicia 38 and 40 are preferably provided to be between medial end 56 and distal ends 58, Bridge 60 at distal end 56 provides additional strength to cannula 10 to resist bending during insertion into foot 14.

Preferably, lines 62, 64, and 66 are provided by laser etching on interior surface 68 of bore 36. Laser etching provides a relatively inexpensive method of providing such a mark at the desired position within bore 36. In the presently preferred embodiment lines 62, 64, and 66 are substantially ring-shaped, or U-shaped. The lines start on one side 70 of slot 48 and extend around bore 36 in a direction orthogonal to axis 54 to end at side 72 of slot 48. It will be understood that other markings or indicia could also be used for this purpose as long as they are durable and capable of being thoroughly sterilized. As well, additional or fewer lines or markings could be used as desired. Lines 62, 64, and 66 are easily visible as by endoscope 26 and provide a quick visual reference for the positioning of blade 34 or another instrument.

In a preferred embodiment, indicia 38 and 40 are provided at positions that are representative of average distances related to the plantar fascia, such as plantar fascia 18, in most people. It is not required that the indicia be positioned in the same manner as shown, but it is believed that these distances generally provide a useful reference. Thus, distance 74 as measured between wall 44 and line 62 is preferably 9 millimeters, distance 76 is preferably 2 millimeters, and distance 78 is preferably 12.5 millimeters as measured. Indicium 38 will generally be positioned at about medial edge 80 of plantar fascia 18, as is about the average position in the population, and indicium 40 will preferably be positioned about one-third of the distance to distal edge 82 of plantar fascia 18, as may indicate a desired approximate incision length. It can be seen that indicia 38 and 40 are easily distinguished from each other by the fact that indicium 38 has two lines 62 and 64 while indicium 40 has only one line 66.

In operation, indicia 38 and 40 can be used as quick reference positions to allow the surgeon to quickly position blade 34 at the desired position by viewing a picture available from endoscope 26. Therefore, the surgeon has a visible frame of reference that allows for quickly positioning his instrument. Because the operation preferably takes only a very short time, this convenience provides an advantage to the surgeon of decreasing the time required in making measurements during the operation while also effectively enhancing the necessary accuracy of the procedure.

The foregoing disclosure and description of the invention is illustrative and explanatory thereof, and it will appreciated by those skilled in the art that various changes in the size, shape, and materials, as well as in the details of the illustrated construction or combinations of features of the various cannula elements, may be made without departing from the spirit of the invention.

What is claimed is:

1. A cannula for receiving an endoscope and a surgical instrument, said cannula comprising:
    a tubular body having an internal surface defining a longitudinal bore extending through said tubular body for receipt of said endoscope and said surgical instrument, said tubular body having a tubular body wall, said tubular body having a tubular longitudinal axis, said tubular defining an elongate slot through said tubular body wall, said elongate slot being parallel with said tubular longitudinal axis; and
    a first indicium disposed at a fixed first position on said internal surface of said longitudinal bore adjacent said elongate slot, said first indicium Permitting the unobstructed receipt of said endoscope for permitting positioning of said surgical instrument at said first position.

2. The cannula of claim 1, further comprising:
    a second indicium disposed at a fixed second position on said internal surface of said longitudinal bore adjacent said elongate slot, said second indicium being axially spaced from said first indicium, said second indicium permitting the unobstructed receipt of said endoscope through said longitudinal bore and being visible through said endoscope for designating said second position on said internal surface of said longitudinal bore.

3. The cannula of claim 2, wherein:

said first indicium and said second indicium are visibly distinctive from each other when viewed with said endoscope.

4. The cannula of claim 3, further comprising:

a flange member disposed on one end of said tubular body substantially orthogonal with respect to said tubular longitudinal axis, said first indicium being medial to said flange member and said second indicium being distal to said flange member, said longitudinal bore having a substantially constant diameter along its length.

5. The cannula of claim 1, wherein:

said first indicium is inscribed by a laser.

6. The cannula of claim 1, wherein:

said first indicium includes a substantially ring-shaped line such that said ring-shaped line defines a plane orthogonal to said tubular longitudinal axis.

7. The cannula of claim 1, wherein:

said first indicium includes two substantially ring-shaped portions such that each of said two ring-shaped portions define a plane orthogonal to said tubular longitudinal axis.

8. The cannula of claim 7, further comprising:

a second indicium disposed at a fixed second position on said internal surface of said longitudinal bore adjacent said elongate slot, said second indicium being axially spaced from said first indicium, said second indicium permitting the unobstructed receipt of said endoscope through said longitudinal bore and being visible through said endoscope for designating said second position on said internal surface of said longitudinal bore, said second indicium including a single substantially ring-shaped portion such that said single ring-shaped portion defines a plane orthogonal to said tubular longitudinal axis.

9. The cannula of claim 1, wherein:

said slot has a medial end and a distal end said first indicium being disposed between said medial and distal ends.

10. The cannula of claim 1, wherein said tubular body has a medial portal and a lateral portal said bore extending through said tubular body between said medial and lateral portals.

11. A cannula for receiving an endoscope and a surgical instrument, said cannula comprising:

A tubular body having an internal surface defining a longitudinal bore extending through said tubular body and a tubular body wall for receipt of said endoscope and said surgical instrument, said tubular body defining an elongate slot through said tubular body wall, said elongate slot being parallel with said longitudinal bore and defining a medial end and a distal end;

a bridge formed between the distal end of the elongate slot and a distal end of the tubular body for providing additional strength to the tubular body; and a first indicium disposed at a fixed first position between the medial end distal ends of said elongate slot and on said internal surface of said longitudinal bore, said first indicium being visible through said endoscope for permitting positioning of said surgical instrument at said first position.

* * * * *